United States Patent
Xanthis et al.

(10) Patent No.: US 12,326,484 B2
(45) Date of Patent: Jun. 10, 2025

(54) METHOD DIRECTED TO MAGNETIC RESONANCE (MR) IMAGING SIMULATION

(71) Applicant: CORSMED AB, Stockholm (SE)

(72) Inventors: Christos Xanthis, Athens (GR); Jorge Fernandez Villena, Lisbon (PT)

(73) Assignee: CORSMED AB, Stockholm (SE)

( * ) Notice: Subject to any disclaimer, the term of this patent is extended or adjusted under 35 U.S.C. 154(b) by 73 days.

(21) Appl. No.: 18/026,219

(22) PCT Filed: Sep. 14, 2021

(86) PCT No.: PCT/SE2021/050880
§ 371 (c)(1),
(2) Date: Mar. 14, 2023

(87) PCT Pub. No.: WO2022/060279
PCT Pub. Date: Mar. 24, 2022

(65) Prior Publication Data
US 2023/0358825 A1    Nov. 9, 2023

(30) Foreign Application Priority Data

Sep. 18, 2020    (SE) .................................... 2051088-9

(51) Int. Cl.
*G01V 3/00* (2006.01)
*A61B 5/055* (2006.01)
(Continued)

(52) U.S. Cl.
CPC .......... *G01R 33/0064* (2013.01); *A61B 5/055* (2013.01); *G01R 33/543* (2013.01); *G01R 33/5608* (2013.01)

(58) Field of Classification Search
CPC .............. G01R 33/0064; G01R 33/543; G01R 33/5608
(Continued)

(56) References Cited

U.S. PATENT DOCUMENTS

| | | |
|---|---|---|
| 9,857,443 B2 | 1/2018 | Tadic et al. |
| 10,585,157 B2 | 3/2020 | De Rochefort |

(Continued)

FOREIGN PATENT DOCUMENTS

| | | | | |
|---|---|---|---|---|
| CN | 103809142 A | * | 5/2014 | ............. G01R 33/50 |
| EP | 2414857 A1 | | 2/2012 | |

(Continued)

OTHER PUBLICATIONS

Xanthis; "Simulator-generated training datasets as an alternative to using patient data for machine learning: An example in myocardial segmentation with MRI"; Computer Methods and Programs in Biomedicine 198 (2021) 105817.

(Continued)

*Primary Examiner* — Walter L Lindsay, Jr.
*Assistant Examiner* — Frederick Wenderoth
(74) *Attorney, Agent, or Firm* — MOSER TABOADA

(57) ABSTRACT

The present invention describes method directed to magnetic resonance (MR) imaging simulation, said method comprising—partitioning a pulse sequence in parts that have RF excitation and parts that do not have RF excitation; —for each of the parts that do not have the RF active, called gradient parts, performing compression of the gradient parts and then representing signals driving the gradients as an accumulation of area until a readout time point; and then performing the simulation.

12 Claims, 2 Drawing Sheets

(51) Int. Cl.
*G01R 33/00* (2006.01)
*G01R 33/54* (2006.01)
*G01R 33/56* (2006.01)

(58) Field of Classification Search
USPC .......................................................... 324/309
See application file for complete search history.

(56) References Cited

U.S. PATENT DOCUMENTS

| | | |
|---|---|---|
| 2010/0004909 A1 | 1/2010 | Nitz |
| 2014/0133725 A1 | 5/2014 | Feiweier |
| 2014/0266198 A1 | 9/2014 | Tadic et al. |
| 2018/0136300 A1 | 5/2018 | DeRochefort |

FOREIGN PATENT DOCUMENTS

| | | |
|---|---|---|
| EP | 3379281 A1 | 9/2018 |
| EP | 3617731 A1 | 3/2020 |
| JP | H-01086951 A | 10/1990 |
| JP | H-0947442 A | 2/1997 |
| JP | 2012522562 A | 9/2012 |
| JP | 2018517152 A | 6/2018 |
| JP | 2018526657 A | 9/2018 |
| JP | 2020513975 A | 5/2020 |
| WO | WO-2008/109783 A2 | 9/2008 |
| WO | WO-2016/145355 A1 | 9/2016 |
| WO | WO-2020/036861 A1 | 2/2020 |

OTHER PUBLICATIONS

Xanthis; "coreMRI: A high-performance, publicly available MR simulation platform on the cloud"; PLOS One; https://doi.org/10.1371/journal.pone.0216594; May 17, 2019.

Selvi; "A rapid compression technique for 4-D functional MRI images using data rearrangement and modified binary array techniques"; Australas Phys Eng Sci Med (2015) 38:731-742.

International Search Report for Application No. PCT/SE2021/050880 dated Nov. 11, 2021.

Xanthis, et al., "MRISIMUL: A GPU-Based Parallel Approach to MRI Simulations", IEEE Transactions on Medical Imaging, vol. 33, No. 3, Mar. 2014, 11 pages.

Lauzon, et al., "A Beginner's Guide to Block Equation Simulations of Magnetic Resonance Imaging Sequences", Depts. Of Radiology and Clinical Neurosciences, University of Calgary, Calgary, AB, Canada, 18 pages.

Mathematics Study Consultation Session 0007—Introduction to Riemann Integration; Ritsumeikan University, College of Science and Engineering, Mathematics Study Consultation Session; Sep. 16, 2015, 31 pages.

\* cited by examiner

METHOD DIRECTED TO MAGNETIC RESONANCE (MR) IMAGING SIMULATION

FIELD OF THE INVENTION

The present invention relates to a method directed to magnetic resonance (MR) imaging simulation.

TECHNICAL FIELD

The present invention is in general directed to advanced MRI simulation without the need for using a real MRI scanner. More specifically, the present invention is directed to a method for magnetic resonance (MR) imaging simulation in which a preferred computer model is used so that a certain thought volume of an object may be analysed in an advantageous way.

SUMMARY OF THE INVENTION

The latter stated purpose above is achieved by a method directed to magnetic resonance (MR) imaging simulation, said method comprising
   partitioning a pulse sequence in parts that have RF excitation and parts that do not have RF excitation;
   for each of the parts that do not have the RF active, called gradient parts, performing compression of the gradient parts and then representing signals driving the gradients as an accumulation of area until a readout time point; and
   then performing the simulation.

The present invention is directed to a method where the parts without RF excitation is focused on. This further implies that the method involves separating out these non-RF parts, which is enabled when the RF transmit is turned off.

Furthermore, as should be understood from above the method according to the present invention involves compression of the gradient parts and then representing signals driving the gradients as an accumulation of area until a readout time point, which implies that the time compression of the sequence is defined as an accumulation of area until a readout time point (see (A, h) pairs below) instead of time-signals. This is a novel feature and concept when compared to known and used methods today.

DESCRIPTION OF THE PRESENT INVENTION AND RELATED TECHNICAL BACKGROUND

Area-Based Sequence Compression for Fast MRI Simulation

Basics of MRI Simulation

MRI technology is based on the visual interpretation of the time evolution of the magnetization of the certain atomic protons (spins) in soft tissue in the presence of a strong constant magnetic field (main field) and when excited by smaller varying magnetic fields.

Therefore, MRI is based on an implicit use of the Spin Dynamics, and the evolution of the magnetization in the presence of an external varying magnetic field is modeled at a macro-scale by the Bloch Equations [1]. Simulation of the MRI phenomena rely on solving Bloch equations (or upgraded derivate versions that incorporate other physics, e.g. Bloch-Torrey for diffusion [2]).

A basic form of Bloch equation for MRI purposes is:

$$dMx(r,t)/dt = \text{gamma}(Bz(r,t)My(r,t) - By(r,t)Mz(r,t)) - Mx(r,t)/T2(r)$$

$$dMy(r,t)/dt = \text{gamma}(Bx(r,t)Mz(r,t) - Bz(r,t)Mx(r,t)) - My(r,t)/T2(r)$$

$$dMz(r,t)/dt = \text{gamma}(By(r,t)Mx(r,t) - Bx(r,t)My(r,t)) - (Mz(r,t) - M0z(r))/T1(r)$$

where:
r is the coordinate of the "spin" or proton;
t is the time;
gamma is gyromagnetic ratio;
Mx(r,t), My(r,t), Mz(r,t) are the cartesian components of the magnetization M(r,t);
dM_(r,t)/dt is the time derivative of the given component of the magnetization;
Bx(r,t), By(r,t), Bz(r,t) are the cartesian components of the external magnetic field B(r,t);
T2(r) is the tissue dependent spin-spin relaxation time;
T1(r) is the tissue dependent spin-lattice relaxation time; and
M0z(r) is the initial (or equilibrium) magnetization.

Basics of MRI

MRI is based on a series of events.

Equilibrium: A constant strong main magnetic field B0 is usually applied in the z direction, which aligns the spins into an initial state M0z (equilibrium), and produces a precession depending on the gyromagnetic ratio. In relation to z, above and below, the z direction is considered the direction of the main magnetic field.

RF Excitation: Short radio-frequency (RF) fields, with transversal (x and y) magnetic components (Bx and By) at the frequency of the precession, are applied in order to perturb the magnetization of the spins, and take it to a specific Mx My and Mz combination.

Encoding and Acquisition: After the RF are turned off, gradient fields in the z component (a Bz that changes with the location) are applied to generate the so called "spatial encoding", so that each voxel has a precession related to its position, and thus there is a difference of the Mx and My magnetizations (the transverse magnetization), which is latter used to create an image.

The combined effect of these transverse magnetization radiates a RF field with x and y components, that is received with a coil using Faradays Law, and transformed into an electric signal S(t)=S(Mx(t),My(t)), where S is a function of the receive coil sensitivities.

Relaxation: (can be either full or partial) no external field is applied, so that the transverse (xy) magnetization will naturally decay due to T2, whereas the Mz magnetization will recover towards M0z with T1 constant.

MRI uses precise timing and a sequence of repetitions of these basic events to acquired time signals S(t). These signals are resolved into an image using knowledge of the encoding, and the type of signals applied will make the signals more or less dependent upon T1 and T2, resulting in natural contrast based on the tissue properties.

Specifics of MRI Simulation

Given that MRI operates under a constant strong static field B0 in the z direction, Bz(t)=B0+ΔBz(t) (where B0 is the constant field value, and ΔBz(t) are variations due to external excitations or inhomogeneities and non-linearities), a typical representation for the simulation of the Bloch equations is based on the rotating frame of reference [4], in which the precession effect of B0 is removed from Bz to simplify the formulation.

The Bx and By fields are due to RF excitation, whereas the Bz fields are due to the effect of the Gradient fields and other effects, such as inhomogeneities due to physical effects (susceptibility, Chemical Shift) or hardware imperfections, so that, once removed the effect of the B0 field, z component of the magnetic field is:

$$Bz(r,t)=\Delta Bz(r)+gx(t)Gx(r)+gy(t)Gy(r)+gz(t)Gz(r)$$

where
ΔBz(r) are the non-idealities;
Gx(r) Gy(r) Gz(r) are the field maps produced by the gradient coils; and
gx(t) gy(t) gz(t) are the time signals of the MRI sequence driving the gradient coils.

In this regard it should also be noted that in a more advanced case, the gradient field maps may be time-varying as well: Gx(r,t) Gy(r,t) Gz(r,t).

The Bloch equation is an Ordinary-Differential Equation (ODE) [3] and can be represented as dM/dt=F(M,B,T1,T2,M0z), where F is a function, and the time and position dependencies are implicit.

ODEs can be numerically solved given an initial solution by temporal discretization, where the time is split in small segments during which the B fields are assumed constant, and the solution of the Magnetization at each time step can be computed iteratively by time integration from previous solutions.

There are different well-known methods that can be applied [3]. For example, using an explicit forward difference scheme, where dt=t(n)−t(n−1), and M(t) at t(n−1) is known, we can solve the differential equation $$(M(t+dt)-M(t))/dt=F(M(t),B,T1,T2,M0z) \text{ to compute } M(t+dt).$$

Alternatively, an analytical solution can be obtained for a constant field time step, by applying a matrix exponential. Given the structure of the Bloch equations, this operation can be decomposed as a series of rotations (depending on the B fields) and exponential decays [4,5], represented in compressed form as:

$$M(t+dt)=E(dt)R(dt)M(t)+Eeq(dt)$$

Where for each time step:
M(t) is the magnetization vector, M(t)=[Mx(t), My(t), Mz(t)]' where [ ]' indicates transpose,
E(dt) is a 3×3 matrix with the exponential decays depending on T1 and T2,
E(dt)=diag(exp(−dt/T2), exp(−dt/T2), exp(−dt/T1))
Eeq(dt) is the longitudinal recovery vector, Eeq(dt)=[0, 0, M0z*(1−exp(−dt/T1))]' with M0z being the equilibrium magnetization.
and R(dt) is a 3×3 rotation matrix, depending on the B fields.

In cartesian components, the effect of the exponential decay operations E(dt) and Eeq(dt) during the interval dt are $$Mx(t+dt)=\exp(-dt/T2)*Mx(t)$$

$$Mx(t+dt)=\exp(-dt/T2)*My(t)$$

$$Mz(t+dt)=M0z+(Mz-M0z)*\exp(-dt/T1)$$

where T1 and T2 are the tissue dependent relaxation constants.

The operations in R(dt) involve a series of rotations, whose angles depends on the B fields during the interval dt. A typical representation [4] decomposes R(dt) into a series of rotations $$R(dt)=Rz(\text{phi})*Rx(-\text{beta})*Ry(\text{alpha})*Rx(\text{beta})*Rz(-\text{phi})$$

where each rotation can be represented in a matrix form $$Rz(\text{phi}) = \begin{matrix} \cos(\text{phi}) & -\sin(\text{phi}) & 0 \\ \sin(\text{phi}) & \cos(\text{phi}) & 0 \\ 0 & 0 & 1 \end{matrix}$$

$$Ry(\text{alpha}) = \begin{matrix} \cos(\text{alpha}) & 0 & \sin(\text{alpha}) \\ 0 & 1 & 0 \\ -\sin(\text{alpha}) & 0 & \cos(\text{alpha}) \end{matrix}$$

$$Rx(\text{beta}) = \begin{matrix} 1 & 0 & 0 \\ 0 & \cos(\text{beta}) & -\sin(\text{beta}) \\ 0 & \sin(\text{beta}) & \cos(\text{beta}) \end{matrix}$$

Other representations and approximations to the same operations are possible [6], which may be advantageous in computational terms for certain situations.

In any case, numerical Bloch simulation relies on a time discretization into small intervals, with constant B fields, and a numerical or analytical time integration based on the magnetization at the beginning of the interval. Note that this is a sequential procedure, in which a new solution requires computing the previous solutions.

For varying fields, the accuracy of the approximation depends on the time step, with the error being smaller as the duration of the interval gets smaller. But since each step needs to be applied to potentially millions of voxels, a fine discretization results in expensive simulations. In situations where the fields remain constant for large periods of time, the solution can be obtained with a single (larger) time step without any loss of accuracy [4].

Note that for most MRI simulations, the only relevant time points at which the Magnetization is needed is during acquisition steps (called READOUTS), or at the beginning and end of the sequence. These are a small fraction of the time points that need to be computed in practice for an accurate simulation.

For practical purposes, in which a 3D Field of View (FOV) containing a biological tissue wants to be simulated, a spatial discretization is also applied, in which the 3D FOV is divided into small voxels. A voxel is a small volume encompassing multiple nuclei with the same tissue properties, and that due to their proximity are assumed to experience the same external fields. Therefore B, M, T1, T2 and M0z are assumed to be constant at each voxel, which is assigned a coordinate r and a volume. The magnetization of this voxel can be simulated with the above procedure. In relation to the above it should be noted that the present invention also covers the case when it is actually more than one tissue type within a single voxel.

Typical Bloch simulation for MRI is based on numerical approaches presented above, where the time is discretized in small discretizing the time domain into small steps Specific Embodiments of the Present Invention and Related Details The present invention is directed to a method involving area-based sequence compression. According to the present invention the inventors propose to apply an alternative representation of the sequence. As a pre-process step, a sequence is partitioned in parts, separating the parts that have RF excitation, and thus time varying Bx, By and Bz fields, and parts that do not have RF excitation (Encoding, Acquisition and Relaxation parts of the sequence), where only time varying Bz fields are present, i.e. Bx(t)=By(t)=0. This can be done by identifying and grouping time steps that have non-zero signals driving the transmit coils. In cases where the sequence is not yet represented using a time discretization, a time discretization can be applied beforehand.

For each of the parts that do not have the RF active, suitably called GRADIENT parts, the signals driving the gradients may be represented as an accumulation of area, A, until the READOUT time point:

A=F(amplitude, h, t), with F a function, and h=t(readout)−t0, and to the initial time of the part and only store these pair of values (A, h) for the times of interest (READOUTS). The area A can be computed by integration of the time signal (either analytically, or numerically using Riemann integral).

Based on the above, according to one specific embodiment of the present invention, referred to as a first embodiment aspect below, the compression of the gradient parts is performed either by a pre-computation of (A, h) pairs where A are signals driving the gradients as an accumulation area until a readout time point, t(readout), and where h is h=t(readout)−t0, with t being time, or on the fly by accruing phase and time.

In line with the above, according to yet another specific embodiment of the present invention signals A driving the gradients as an accumulation area until the readout time point are presented as the integral of the signal amplitude over time, preferably numerically approximated, such as by A=Sum_i(dt*amplitude(t_i)), with t_i=t(i), dt=t(i)−t(i−1), for i in the discrete interval [1, readout].

Once one has represented the sequence at each GRADIENT part as a set of AREAS (A) and PERIODS (h), the simulation may be performed. Note that the product gamma*A*Gradient provides the phase accrued due to the corresponding signals, and thus the rotation due to the Bz field corresponds to:

$$PHI(r)=gamma*(h*\Delta Bz(r)+Ax*Gr(r)+Ay*Gy(r)+Az*Gz(r))$$

where r is the coordinate of the "spin" or proton, $\Delta Bz(r)$ is the position dependent non-linear field effects, Gx(r) Gy(r) and Gz(r) are the spatial distribution of the z component of the magnetic field (Bz) due to gradient coils, and PHI(r) is the position dependent angle to rotate during the time period h, with Ax, Ay and Az the AREAS computed by time integration of each of the gradient signals gx(t), gy(t) and gz(t).

Moreover, in this case, it is possible to compute a solution of the magnetization at each of the READOUT points, given an initial magnetization (M0) at the beginning of the GRADIENT part (t0), with a single step consisting of a rotation and an exponential decay applied to the initial magnetization M0 at the beginning of the GRADIENT sequence part.

Based on the above, according to one specific embodiment of the present invention, the method is performed by performing the following:

For each readout at time t, with h=t−t0:
Compute the decays and rotations:

$$E(h), R(PHI), Eeq(h)$$

Apply them to M(t0) to obtain the solution at the readout time t:

$$M_{READOUT}(t)=E(h)R(PHI)M(t0)+Eeq(h)$$

where E(h) and Eeq(h) are the effect of the relaxation constants T1 and T2 during the period h, and R(PHI) is the rotation due to the accumulation of the phase, directly related to the Bz field.

In this case, since one only has a z component of the field, the rotation is a rotation around the z axis:

$$Rz(PHI) = \begin{matrix} cos(PHI) & sin(PHI) & 0 \\ -sin(PHI) & cos(PHI) & 0 \\ 0 & 0 & 1 \end{matrix}$$

Therefore $M_{READOUT}(t)=E(h)R(PHI)M(t0)+Eeq(h)$ can be represented in cartesian components as $$Mx(t)=exp(-h/T2)*(cos(PHI)*Mx(t0)+sin(PHI)*My(t0))$$

$$My(t)=exp(-h/T2)*(-sin(PHI)*Mx(t0)+cos(PHI)*My(t0))$$

$$Mz(t)=M0z+(Mz(t0)-M0z)*exp(-h/T1)$$

where Mx(t0), My(t0), and Mz(t0) are the initial conditions at the beginning of the GRADIENT part (t0).

Note that without compression, one needs to compute the solution in an iterative fashion instead:

$$M(t0+dt)=E(dt)R(dt)M(t0)$$

$$M(t0+2dt)=E(dt)R(dt)M(t0+dt)$$

$$M(t0+h)=E(dt)R(dt)M(t0+h-dt)$$

Moreover, note that the iterative procedure is equivalent to partition of the signal in piecewise constant steps of duration dt, and apply the rotation of the area associated to that small step.

$$R(dt)=R(Rho)$$

with $$Rho(r)=gamma*dt*(\Delta Bz(r)+gx(t=ti)*Gx(r)+gy(t=ti)*Gy(r)+gz(t=ti)*Gz(r))$$

In a sense, the traditional (iterative) approach is conceptually akin to apply the Riemann integral using the individual rotations and decays of each step.

Furthermore, below there is provided a set of implications and advantages with the concept according to the embodiments of the first aspect of the present invention disclosed above:

1) A pre-computation is required to reformulate the sequence gx(t), gy(t) and gz(t) as a set of pairs (A, h) with area and duration, for each point of interest (READOUTS and end point of the part). This is very efficient and cheap since it only needs to process the sequence, and only needs to be done once per sequence.
2) The accuracy of the computation of the area can be arbitrarily controlled. For analytical integration is exact; for numerical integration the discretization of the time signal can be refined without impact in the performance of the actual simulation.
3) Instead of needing to apply the numerical simulation on a large number of time steps with dt discretization, we only need to apply the rotation and decay once for each of the point of interest (READOUTS). This is particularly relevant for realistic waveforms (trapezoidal) or more advance encodings, for example spirals that employ sinusoidal waveforms, and that would require a fine discretization for high accuracy. This results in a big performance boost, in particular since realistic simulations may have to apply these operations on millions of voxels.

4) The solution at each READOUT only depends on the initial solution M(t0) at the beginning of the GRADIENT part, and its (A,h). Therefore, the solution for each READOUT can be computed in parallel employing multiple computer machines or computer cores. This further increases the potential performance improvement. Based on this, according to one specific embodiment, the simulation for each readout time point is performed in parallel once the (A, h) pairs have been pre-computed.
5) The RF parts still need to be simulated in a conventional way. And the simulation of the parts needs to be sequential: the initial M(t0) for each GRADIENT part is only available when the previous parts have been simulated.
6) The effects of magnetic field inhomogeneities or other effects can be accounted as a constant (or time varying if applicable) signal, and can be included as shown above for each READOUT as gamma*h*ΔBz(r)

According to a second embodiment aspect of the present invention, there is an alternative representation of the Magnetization, and thus of the Bloch equation, applied. Instead of representing the system in cartesian coordinates, we propose to use polar coordinates, representing the transverse magnetization as a time dependent phasor. Therefore, according to one embodiment of the present invention, said method also comprising representing transverse magnetization as a time dependent phasor and thus representing a system in polar coordinates.

With magnitude (Mm) and phase (φ), the following may apply:

$$Mxy = Mm \exp(i\varphi).$$

where Mxy is the transversal magnetization, and i is the complex unit.

There is a clear relation between the cartesian and polar components:

$$Mx = \mathrm{real}(Mxy) = Mm \cos(\varphi)$$

$$My = \mathrm{imag}(Mxy) = Mm \sin(\varphi)$$

$$Mz = Mz.$$

There are some advantages using this representation. Similar to the case of the first embodiment aspect disclosed above, when we are simulating time points that do not have active RF (Bx(t)=By(t)=0), the computation for the simulation of a step dt reduces to $$\varphi(t+dt) = \varphi(t) - \mathrm{gamma}^* dt^* (\Delta Bz(r) + gx(t=ti)^* Gx(r) + gy(t=ti)^* Gy(r) + gz(t=ti)^* Gz(r))$$

$$Mm(t+dt) = Mm(t)^* \exp(-dt/T2(r))$$

$$Mz(t+dt) = M0z + (Mz(t) - M0z)^* \exp(-dt/T1(r)).$$

Based on the above, according to yet another embodiment of the present invention the method involves avoiding computing the exponentials by accumulating the time if a time point is not a time point of interest, preferably by use of the following requirements:

If READOUT:

$$\varphi\mathrel{-}= \mathrm{gamma}^* dt^* (\Delta Bz(r) + gx(t=ti)^* Gx(r) + gy(t=ti)^* Gy(r) + gz(t=ti)^* Gz(r))$$

$$Mm = Mm(t0)^* \exp(-h/T2(r))$$

$$Mz = M0z + (Mz(t0) - M0z)^* \exp(-h/T1(r))$$

ELSE:

$$\varphi\mathrel{-}= \mathrm{gamma}^* dt^* (\Delta Bz(r) + gx(t=ti)^* Gx(r) + gy(t=ti)^* Gy(r) + gz(t=ti)^* Gz(r))$$

$$h\mathrel{+}= dt.$$

Therefore, according to yet another embodiment, the method involves tracking of a spatial derivate of the phase with respect to the spatial direction, preferably as extra variables according to the following:

$$d\varphi/dx \mathrel{-}= \mathrm{gamma}^* dt^* (d\Delta Bz(r)/dx + gx(t=ti)^* dGx(r)/dx)$$

$$d\varphi/dy \mathrel{-}= \mathrm{gamma}^* dt^* (d\Delta Bz(r)/dy + gy(t=ti)^* dGy(r)/dy)$$

$$d\varphi/dz \mathrel{-}= \mathrm{gamma}^* dt^* (d\Delta Bz(r)/dz + gz(t=ti)^* dGz(r)/dz).$$

This is useful for some relevant cases, namely capture the variation of the phase over the voxel to remove spurious echoes (which requires the phase integration over a voxel), or to compute the effect of the Diffusion, which needs these derivatives [6].

Below there is provided implications and advantages with the concept according to this second embodiment aspect of the present invention disclosed above.

1) There are cases where the sequence compression according to the first embodiment aspect as disclosed above cannot be applied, and where this approach can be useful. For example, in models with motion or flow [5], the position of a voxel change over time. Instead of applying more complex approaches, the phase accrued can be easily accumulated even if the voxel position r changes over time. This movement can be tracked very accurately with small time steps, generating a lot of time points that are not points of interest. Whenever the magnetization needs to be computed (point of interest), the phase and time step accumulated can be used to generate the signal.
2) Performance improvement: in such cases where the approach according to the first aspect cannot be applied, the computation is highly reduced since we do not need to compute the exponentials or the rotations (which require to evaluate sin and cos). This are operations that are much more expensive than the simple products and sums.
3) By keeping track of the phase over time, effects due to the phase variation over the voxel can be easily accounted for. With cartesian coordinates, the actual phase is lost, and can only be obtained in the [0, 2π] or [−π, π] intervals. This can create phase wrapping which is difficult to deal with, and that can limit the correct computation of Diffusion and other phase effects.

It should be understood that both concepts and approaches as explained above can be applied independently, or can be combined, according to the present invention.

When combined, the phase accumulation directly comes from the precomputed area A for each signal.

$$\varphi(r) = \mathrm{gamma}^* (h^* \Delta Bz(r) + Ax^* Gx(r) + Ay^* Gy(r) + Az^* Gz(r))$$

where Ax, Ay and Az are the area integration of the gradient signals during the period h.

And in this case, we will only need to compute the READOUT time points:

For each READOUT:

$$\varphi = \varphi(t0) - \mathrm{gamma}^* (h^* \Delta Bz(r) + Ax^* Gx(r) + Ay^* Gy(r) + Az^* Gz(r))$$

$$Mm = Mm(t0)^* \exp(-h/T2(r))$$

$$Mz = M0z + (Mz(t0) - M0z)^* \exp(-h/T1(r))$$

where Mm(t0), φ(t0), and Mz(t0) are the initial conditions at the beginning of the GRADIENT part (t0).

DESCRIPTION OF THE DRAWINGS

Below there is described a representation of one embodiment according to the present invention, as compared to state of the art today, and with reference to the attached figures.

For a traditional Bloch simulation, for each time point t, with dt=t(n)−t(n−1), then the following is performed:

Compute: $E(dt), Eeq(dt), R(dt)$ $M(t+dt)=E(dt)R(dt)M(t)+Eeq(dt).$

Figure 1:
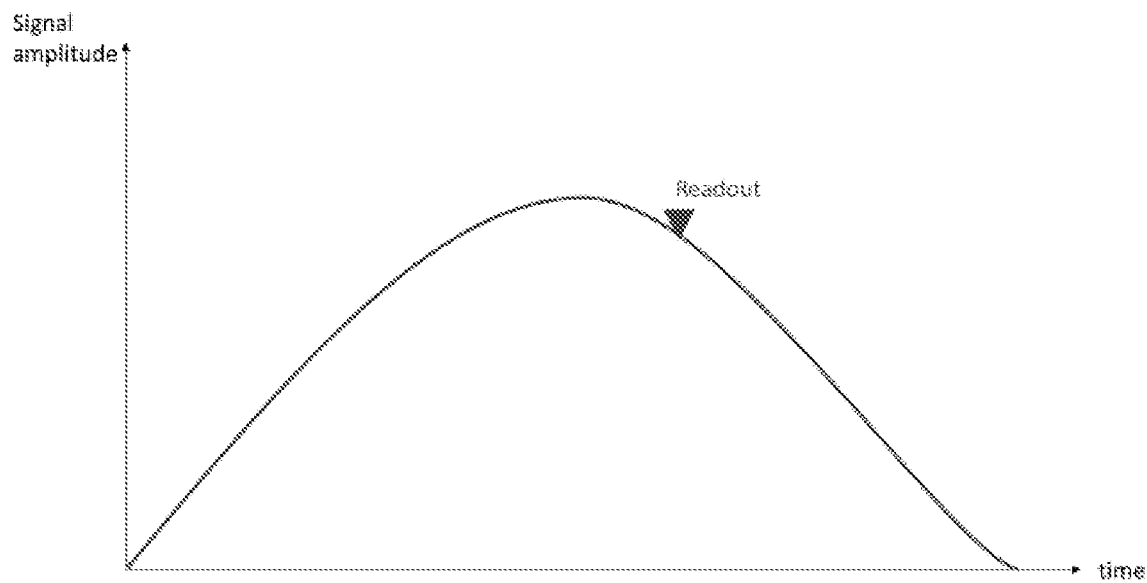
In FIG. 1 there is shown a general relationship for the signal amplitude against time and a though readout point.
Figure 2:
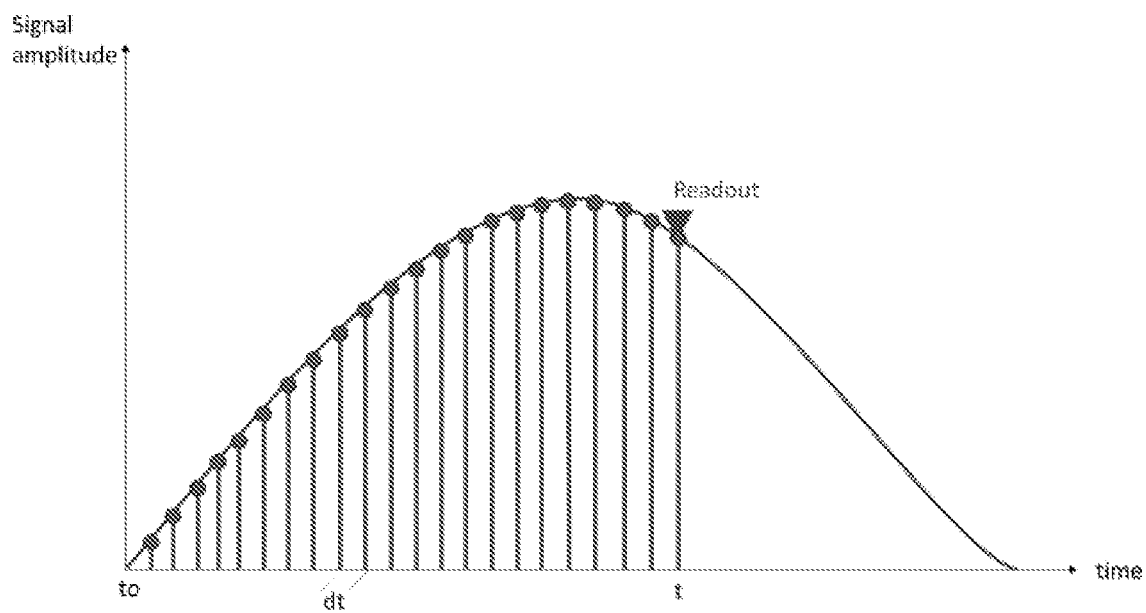

This known alternative is shown in FIG. 2.

Figure 3:
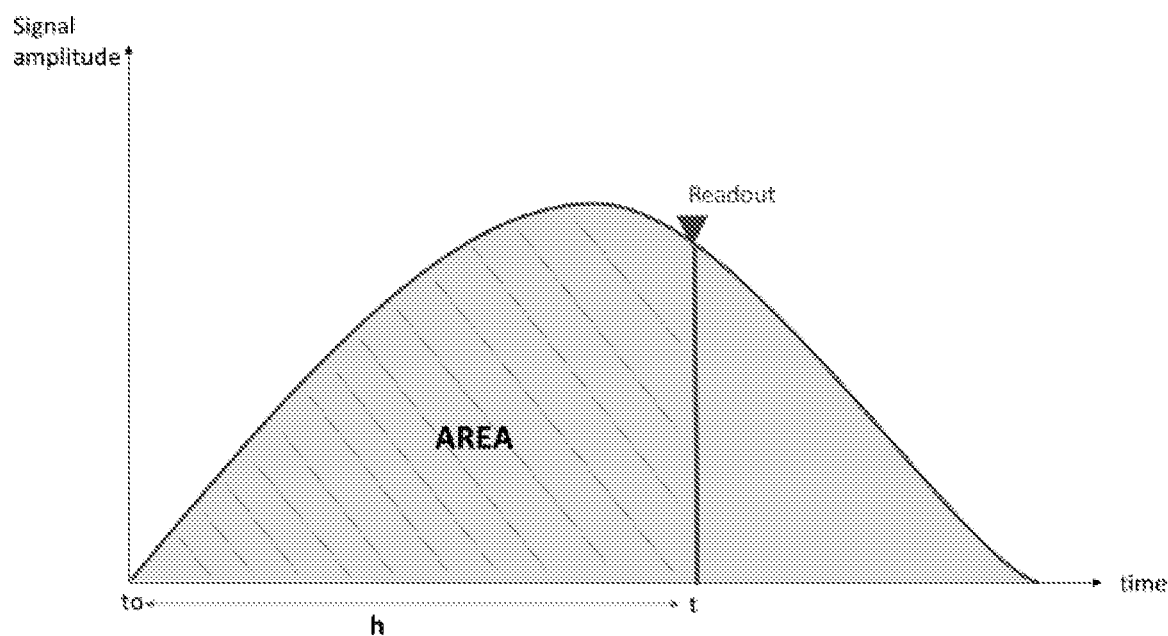

In FIG. 3 there is shown the implication one embodiment according to the present invention, and with the proposed Bloch simulation. According to the present invention, for each Readout at time t, with h=t−to, the following is performed:

Compute: $E(h), Eeq(h), R(AREA)$ $M(t)=E(h)R(AREA)M(t0)+Eeq(h).$

Figure 4:
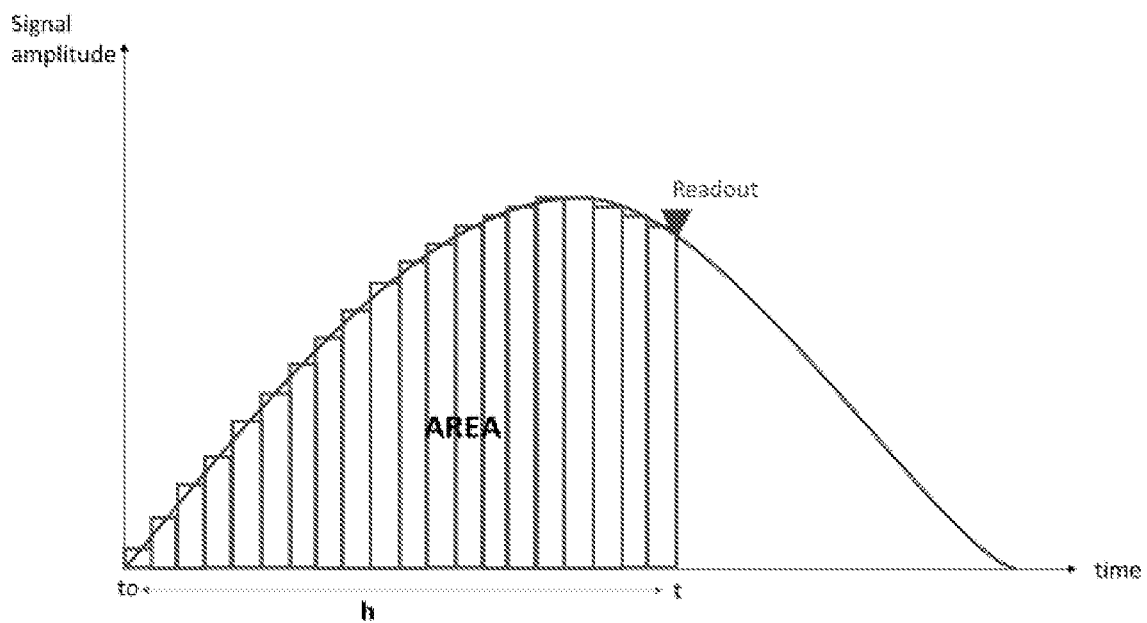

In FIG. 4 there is shown one possible continuation of the embodiment according to the present invention, as shown in FIG. 3. In FIG. 4 there is shown the illustration of a Riemann integral. Here it should be noted that the area is computed as the summation of individual areas.

REFERENCES

[1] F. Bloch, "Nuclear induction", Physical review, 70:460-474, 1946.
[2] H. C. Torrey, "Bloch Equations with Diffusion Terms", Physical review, 104:563-565, 1956.
[3] A. Hazra, "Numerical Simulation of Bloch Equations for Dynamic Magnetic Resonance Imaging", Ph.D. Dissertation, Georg-August-Universität Göttingen, 2016.
[4] C. G. Xanthis, I. E. Venetis, A. V. Chalkias, A. H. Aletras, "MRISIMUL: a GPU-based parallel approach to MRI simulations", IEEE Trans. Med. Imaging 33: 607-616, 2014.
[5] C. G. Xanthis, I. E. Venetis, A. H. Aletras, "High performance MRI simulations of motion on multi-GPU systems", J. Cardiovasc. Magn. Reson. 16:48-62, 2014.
[6] T. H. Jochimsen, A. Schafer, R. Bammer, and M. E. Moseley, "Efficient simulation of magnetic resonance imaging with Bloch-Torrey equations using intra-voxel magnetization gradients," J. Magn. Reson., 180:29-38, 2006.

The invention claimed is:

1. A computer-implemented method comprising magnetic resonance (MR) imaging simulation, said method comprising:

partitioning, by at least one computer, a pulse sequence in parts that have RF excitation and parts that do not have RF excitation;

for each of the parts that do not have the RF active, called gradient parts, using the at least one computer for performing compression of the gradient parts and then representing signals driving the gradients as an accumulation of area until a readout time point;

resolving, by the at least one computer, the representing signals into an image using one or more simulations; and presenting, by the at least one computer, the image on a user interface.

2. The method according to claim 1, wherein the compression of the gradient parts is performed either by a pre-computation of (A, h) pairs where A are signals driving the gradients as an accumulation area until a readout time point, t(readout), and where h is h=t(readout)−t0, with t being time, or on the fly by accruing phase and time.

3. The method according to claim 1, wherein the method is performed by performing the following:

For each readout at time t, with h=t−t0:

Compute: $E(h), R(PHI), Eeq(h)$ $M_{READOUT}(t)=E(h)R(PHI)M(t0)+Eeq(h)$ where M is magnetization vector, t is time, E and Eeq are the effects of relaxation constants T1 and T2 during the time t, and R(PHI) is the rotation due to accumulation of the phase and wherein the following is applied:

M=[Mx, My, Mz]' where [ ]' indicates transpose, and E(h) and R(PHI) are 3×3 matrices according to the following:

$E(h)=\mathrm{diag}(\exp(-h/T2), \exp(-h/T2), \exp(-h/T1))$ and where R(PHI) has the rotations and Eeq(h) is a vector with Eeq(h)=[0, 0, M0z*(1−exp(−h/T1))]' with M0z being the equilibrium magnetization.

4. The method according to claim 1, wherein signals A driving the gradients as an accumulation area until the readout time point are presented as the integral of the signal amplitude over time, preferably numerically approximated, such as by A=Sum_i(dt*amplitude (t_i)), with t_i=t(i), dt=t(i)−t(i−1), for i in the discrete interval [1, readout].

5. The method according to claim 4, wherein the product gamma*A*Gradient provides the phase accrued due to corresponding signals, and where the rotation due to Bz fields, Bz fields being magnetic fields in the z component which are due to gradient fields and other effects but not RF excitation, corresponds to:

PHI(r)=gamma*(h*ΔBz(r)+Ax*Gx(r)+Ay*Gy(r)+ Az*Gz(r))

where r is the coordinate of the "spin" or proton, ΔBz(r) represents the spatial distribution of the field non-linearities, Gx(r) Gy(r) and Gz(r) are the spatial distribution of the z component of the magnetic field (Bz) due to gradient coils, and Ax, Ay and Az are the AREAS computed by time integration for each of the gradient signals gx(t), gy(t) and gz(t).

6. The method according to claim 5, wherein the simulation for each readout time point is performed in parallel once the (A, h) pairs have been pre-computed.

7. The method according to claim 1, said method also comprising representing transverse magnetization as a time dependent phasor and thus representing a system in polar coordinates.

8. The method according to claim 7, wherein the method involves using the following relationship:
if
Mxy=Mm exp(i φ) where Mm is magnitude and φ is phase, and i is the complex unit,
then $$Mx=real(Mxy)=Mm\ cos(\varphi)$$

$$My=imag(Mxy)=Mm\ sin(\varphi)$$

$$Mz=Mz.$$

9. The method according to claim 7, wherein computation of the simulation of the interval dt is based on:

$$\varphi(t+dt)=\varphi(t)-gamma^*dt^*(\Delta Bz(r)+gx(t=ti)^*Gx(r)+gy(t=ti)^*Gy(r)+gz(t=ti)^*Gz(r))$$

$$Mm(t+dt)=Mm(t)^*\exp(-dt/T2(r))$$

$$Mz(t+dt)=M0z+(Mz(t)-M0z)^*\exp(-dt/T1(r)).$$

10. The method according to claim 8, wherein the method involves avoiding computing the exponentials by accumulating the time if a time point is not a time point of interest, preferably by use of the following requirements:
If READOUT:

$$\varphi-=gamma^*dt^*(\Delta Bz(r)+gx(t=ti)^*Gx(r)+gy(t=ti)^*Gy(r)+gz(t=ti)^*Gz(r))$$

$$Mm=Mm(t0)^*\exp(-h/T2(r))$$

$$Mz=M0z+(Mz(t0)-M0z)^*\exp(-h/T1(r))$$

else:

$$\varphi-=gamma^*dt^*(\Delta Bz(r)+gx(t=ti)^*Gx(r)+gy(t=ti)^*Gy(r)+gz(t=ti)^*Gz(r))$$

$$h+=dt.$$

11. The method according to claim 7, wherein the method involves tracking of a spatial derivate of the phase with respect to the spatial direction, preferably as extra variables according to the following:

$$d\varphi/dx-=gamma^*dt^*(d\Delta Bz(r)/dx+gx(t=ti)^*dGx(r)/dx)$$

$$d\varphi/dy-=gamma^*dt^*(d\Delta Bz(r)/dy+gy(t=ti)^*dGy(r)/dy)$$

$$d\varphi/dz-=gamma^*dt^*(d\Delta Bz(r)/dz+gz(t=ti)^*dGz(r)/dz).$$

12. The method according to claim 7, wherein the method involves a time dependence of the position of the voxel, ri=r(t=ti), in order to track voxel movement:
If READOUT:

$$\varphi-=gamma^*dt^*(\Delta Bz(ri)+gx(t=ti)^*Gx(ri)+gy(t=ti)^*Gy(ri)+gz(t=ti)^*Gz(ri))$$

$$Mm=Mm(t0)^*\exp(-h/T2(r))$$

$$Mz=M0z+(Mz(t0)-M0z)^*\exp(-h/T1(r))$$

else:

$$\varphi-=gamma^*dt^*(\Delta Bz(ri)+gx(t=ti)^*Gx(ri)+gy(t=ti)^*Gy(ri)+gz(t=ti)^*Gz(ri))$$

$$h+=dt$$

and $$d\varphi/dx-=gamma^*dt^*(d\Delta Bz(ri)/dx+gx(t=ti)^*dGx(ri)/dx)$$

$$d\varphi/dy-=gamma^*dt^*(d\Delta Bz(ri)/dy+gy(t=ti)^*dGy(ri)/dy)$$

$$d\varphi/dz-=gamma^*dt^*(d\Delta Bz(ri)/dz+gz(t=ti)^*dGz(ri)/dz).$$

* * * * *